United States Patent
Presura

(10) Patent No.: US 9,681,812 B2
(45) Date of Patent: Jun. 20, 2017

(54) OPTICAL DEVICE FOR MEASURING A HEART RATE OF A USER

(71) Applicant: KONINKLIJKE PHILIPS N.V., Eindhoven (NL)

(72) Inventor: Cristian Nicolae Presura, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/110,121

(22) PCT Filed: Jan. 22, 2015

(86) PCT No.: PCT/EP2015/051179
§ 371 (c)(1),
(2) Date: Jul. 7, 2016

(87) PCT Pub. No.: WO2015/117829
PCT Pub. Date: Aug. 13, 2015

(65) Prior Publication Data
US 2016/0331251 A1 Nov. 17, 2016

(30) Foreign Application Priority Data
Feb. 4, 2014 (EP) .................................... 14153738

(51) Int. Cl.
*A61B 5/024* (2006.01)
*A61B 5/00* (2006.01)

(52) U.S. Cl.
CPC ...... *A61B 5/02427* (2013.01); *A61B 5/02438* (2013.01); *A61B 5/6824* (2013.01);
(Continued)

(58) Field of Classification Search
CPC . A61B 5/02427; A61B 5/6824; A61B 5/7214; A61B 5/02438; A61B 2560/0242; A61B 2560/0209
See application file for complete search history.

(56) References Cited

U.S. PATENT DOCUMENTS 5,285,784 A 2/1994 Seeker
6,449,501 B1 9/2002 Reuss
(Continued)

FOREIGN PATENT DOCUMENTS

EP 1297784 A1 4/2003
EP 1354553 A1 10/2003
(Continued)

OTHER PUBLICATIONS

Asare, et al., "Clinical Measurements with multi-spectral photoplethysmography sensors", Proc. of SPIE, vol. 8427, (Abstract).
Jonsson, "New Sensor Design Made to Discriminate Between Tissue Blood Flow at Different Tissue Depths at the Sacral Area", Department of Computer Science and Electronics, Malardalen University, Vasteras, Apr. 18, 2006 (Abstract).
(Continued)

*Primary Examiner* — Peter Luong

(57) ABSTRACT

The invention relates to an optical device for measuring a heart rate of a user. Said optical device comprises: —two light sources (1,2) for emitting light into the skin of the user, —a sensor (3) for sensing the light signals emitted by each of the two light sources and reflected through the skin of the user so as to determine the heart rate of the user. The two light sources (1,2) are situated at different distances from the sensor such that the light signals received from each of the two light sources have a different penetration depth into the skin.

11 Claims, 2 Drawing Sheets

(52) U.S. Cl.
   CPC .... *A61B 5/7214* (2013.01); *A61B 2560/0209* (2013.01); *A61B 2560/0242* (2013.01); *A61B 2562/0242* (2013.01)

(56) References Cited

U.S. PATENT DOCUMENTS

| | | |
|---|---|---|
| 7,043,287 B1 | 5/2006 | Khalil et al. |
| 2012/0283535 A1 | 11/2012 | Sarussi |
| 2013/0324809 A1 | 12/2013 | Lisogurski et al. |
| 2015/0088431 A1* | 3/2015 | Podhajsky ........... A61B 5/0059 702/19 |

FOREIGN PATENT DOCUMENTS

| | | |
|---|---|---|
| JP | 2005160641 A | 6/2005 |
| WO | 9822018 A1 | 5/1998 |

OTHER PUBLICATIONS

Asare, et al., "Multi-spectral photoplethysmography biosensor", Institute of Atomic Physics and Spectroscopy, University of Latvia (Abstract).

Hagblad, "Non-Invasive Techniques for Assessment of Peripheral Blood Flow at Different Vascular Depths", Malardalen University Press Licentiate Theses, 2011.

Naslund, et al., "Non-Invasive continuous estimation of blood flow changes in human patellar bone", Med Bio Eng Comp (2006), 44:501-509.

Shaltis, "Analysis and validation of an artifact resistant design for oxygen saturation measurement using photo pletyhsmographic ring sensors", Massachusetts Institute of Technology, 2004 (Abstract).

Neuschwander, et al., "Mild External Compression of the Leg Increases Skin and Muscle Microvascular Blood Flow and Muscle Oxygenation during Simulated Venous Hypertension", ISRN Vascular Medicine, vol. 2012, Article ID930913, 6 pages.

* cited by examiner $I_1(t) = a_1*p(t) + b_1*m(t)$ $I_2(t) = a_2*p(t) + b_2*m(t)$

OPTICAL DEVICE FOR MEASURING A HEART RATE OF A USER

CROSS-REFERENCE TO PRIOR APPLICATIONS

This application is the U.S. National Phase application under 35 U.S.C. §371 of International Application No. PCT/EP2015/051179, filed on Jan. 22, 2015, which claims the benefit of European Patent Application No. 14153738.1 filed on Feb. 4, 2014. These applications are hereby incorporated by reference herein, for all purposes.

FIELD OF THE INVENTION

The invention relates to an optical device for measuring a heart rate of a user.

BACKGROUND OF THE INVENTION

The principle of optical heart rate measurement is based on the use of a light source that emits light into the skin of a user. Such a measurement is called photoplethysmography (PPG). The emitted light is scattered within the skin, where it is absorbed partially by blood. Reflected light exits the skin and is captured by a sensor. The amount of the signal on the sensor is an indication of the blood volume. The blood volume in the skin changes when the blood stream pulsates and, as a consequence, the signal on the sensor changes directly in response to the pulsation. Hence, the sensor measures directly a pulse of the user in the skin and can thus determine the actual heart rate of the user at a given moment.

The measurement of the heart rate becomes more complex when the user is in motion. Such a motion, even slight, generates motion artefact, which can be defined as a noise signal on top of the pulse signal. Therefore, in order to obtain a highly reliable heartbeat measurement, the motion artefact should be eliminated from the measured pulse signal.

European patent application EP1354553 discloses an apparatus for detecting a heartbeat by using photoplethysmography, and which is capable of detecting the heartbeat even under motion of a user. Such an apparatus comprises a filtering unit for selectively passing only a signal within a specific frequency band among the PPG signal detected by the PPG sensor unit. Such a solution is quite complex and might not always be reliable.

SUMMARY OF THE INVENTION

It is an object of the present invention to propose an optical device for measuring a heart rate of a user that has better performances than the one of the prior art. The invention is defined by the independent claim; the dependent claims define advantageous embodiments.

In accordance with the invention, it is proposed an optical device for measuring a heart rate of a user, said device comprising:
  two light sources for emitting light into the skin of the user,
  a sensor for receiving light signals from the light emitted by each of the two light sources and reflected through the skin of the user so as to determine the heart rate of the user.
The two light sources are situated at different distances from the sensor such that the light signals received from each of the two light sources have a different penetration depth into the skin.

In such a configuration, the light signals emitted by each of the two light sources interfere at different depths with blood vessels. Therefore, such an optical device makes it possible to use two light sources so as to create two light signals interfering with different blood vessels, and to combine the light signals received from the two light sources such that motion artefacts are substantially eliminated and heart rate can assessed reliably.

In accordance with a first embodiment of the invention, the optical device comprises a temperature sensor for measuring an ambient temperature and a control unit for selecting one of the light sources in dependence on the measured ambient temperature. This makes it possible to select one light source depending on a relevant criterion.

In accordance with another embodiment of the invention, the light signals emitted by the two light sources may have an identical or similar wavelength. In accordance with another embodiment of the invention, the light signals emitted by two light sources may also have different wavelengths.

In accordance with still another embodiment of the invention, one light source is lift up with respect to the surface of the skin of the user.

These and other aspects of the invention will be apparent from and elucidated with reference to the embodiments described hereinafter.

BRIEF DESCRIPTION OF THE DRAWING

The present invention will now be described in more detail, by way of example, with reference to the accompanying drawing, wherein.

DETAILED DESCRIPTION OF THE INVENTION

The present invention relates to an optical device for measuring the heart rate of a user. Said device comprises at least two light sources for emitting light into the skin of the user, and a sensor for receiving light signals from the light emitted by each of the two light sources and reflected through the skin of the user so as to determine the heart rate of the user. The optical device comprises a processing unit for receiving the sensor-signal and for determining the pulse and/or heart rate of the user in response to the sensor-signal. According to the invention, the two light sources are situated at different distances from the sensor such that the light signals received from each of the two light sources have a different penetration depth into the skin. The waveforms of said light signals can be made different in terms of amplitude and/or phase. This and other aspects of the invention will be explained in more details in the following embodiments. In the different embodiments, the two light sources are as an example two Light Emitting Devices LEDs. Alternatively, the light sources can also be lasers. In the following, the sensor is also preferably a photo-detector diode. It may also be a phototransistor. The optical device can be in the form of a watch, which is worn at a wrist or arm of the user.

Figure 1:
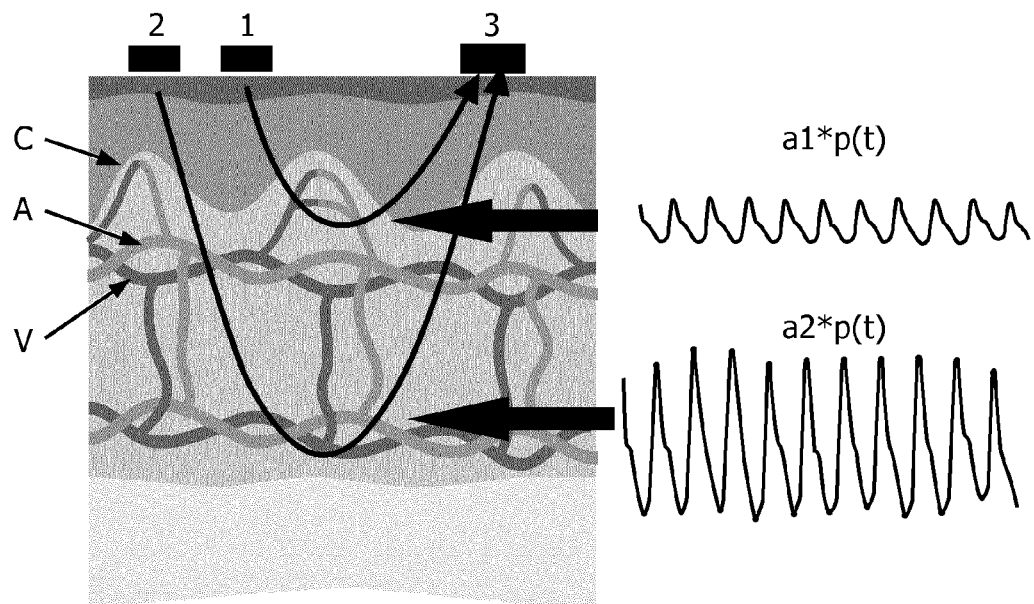
FIG. 1 shows the operation of an optical device according to a first embodiment of the invention.

According to a first embodiment of the invention, as shown in FIG. 1, it is proposed to use the lights emitted by two LEDs having identical wavelength. The two LEDs 1 and 2 emit light into the skin of a user. The two LEDs 1 and 2 are for example two green LEDs. The emitted light is scattered within the skin, where it is absorbed partially by blood depending how deep the emitted light interferes with the blood vessels such as capillary loop C, arteriole A and venule V. The reflected light exits the skin and is captured by a photo-detector diode 3. In the present embodiment, it can be seen on FIG. 1 that the two LEDs 1 and 2 are located at different distances from the photo-detector diode 3. Since the distances between each of the two LEDs 1 and 2 and the photo-detector diode 3 are different, this creates different penetration depths for the light that reaches the photo-detector diode 3. The two LEDs 1 and 2 are pulsed at different times and synchronized with the photo-detector diode 3, and the signals from both depths can be measured simultaneously. In FIG. 1, signal a1*p(t) represents the small pulse signal received from the LED 1 and signal a2*p(t) represents the large pulse signal received from the LED 2, both pulse signals being used to determine the heart rate, and a1 and a2 being constants depending on blood absorption. One advantage of such configuration of LEDs and photo-detector diode is that the amplitude of the pulse signal depends on the penetration depth of said signal. The deeper the blood vessels, the larger the pulse signal. The more shallow that blood vessels, the lower the signal, because those vessels are mostly capillaries and do not bare much of the heart rate signal.

Figure 2:
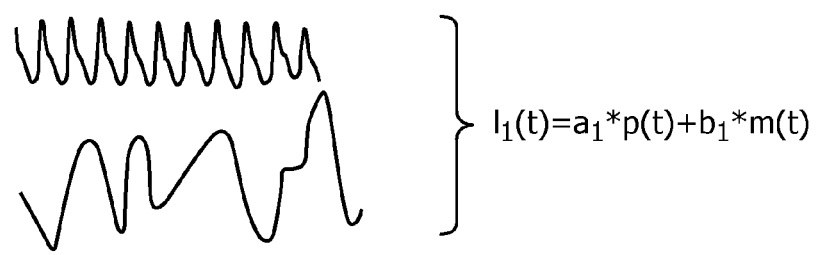
FIG. 2 shows how the pulse component and the motion artefact component are combined to obtain the light signal received by the sensor in accordance with the configuration of light sources of the first embodiment.
Figure 2:
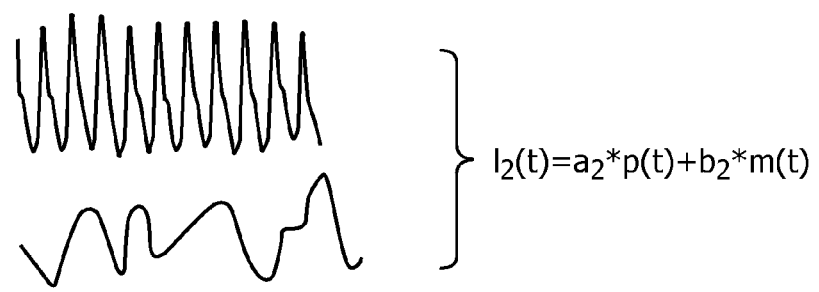

As explained before, the measurement of the heart rate is more complex when the user is in motion, in which case a motion artefact signal is added to the pulse signal. This is illustrated in FIG. 2 where we can see that the resulting light signal I(t) received by the photo-detector diode is the sum of the pulse signal p(t) and the motion artefact signal m(t). More specifically, the first light signal I1(t) received from the first LED is the sum of the small pulse signal a1*p(t) and the first motion artefact signal b1*m(t), and the second light signal I2(t) received from the second LED is the sum of the large pulse signal a2*p(t) and the second motion artefact signal b2*m(t). It is clear from FIG. 2 that motion artefacts are present in both light signals but the motion artefact signal has much more influence on the small pulse signal than on the large pulse signal. As a matter of fact the two motion artefact signals are quite similar. This is because the color of the two LEDs is identical and light travels the same side of the detector. Therefore the invention makes it possible to mix in different ratios the pulse component and the motion artefact component of the light signal, both measured in reflectivity.

Figure 3:
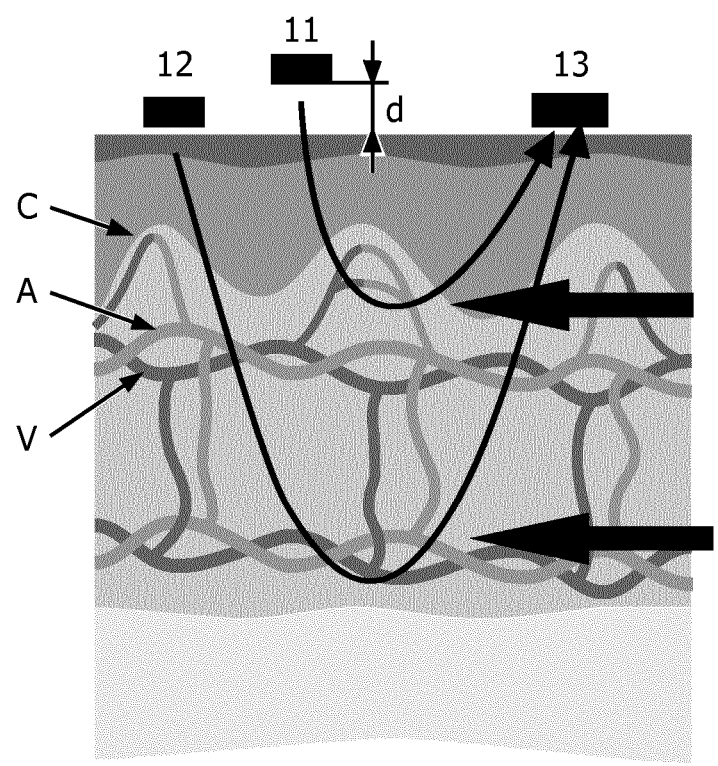
FIG. 3 shows the operation of an optical device according to a second embodiment of the invention.

According to a second embodiment of the invention as shown in FIG. 3, it is proposed to lift up one of the LED with respect to the surface of the skin of the user. On FIG. 3, the first LED 11 which is the closest to the photo-detector diode has been lift up.

As in the first embodiment, two LEDs 11 and 12 emit light into the skin of a user but in the second embodiment, the LED 11 is lift up of a distance d with respect to the surface of the skin of the user. The two LEDs 11 and 12 are also for example two green LEDs. As explained before, the emitted light is scattered within the skin, and it is absorbed partially by blood depending how deep the emitted light interferes with the blood vessels such as capillary loop C, arteriole A and venule V. The reflected light exits the skin and is captured by a photo-detector diode 13. According to this second embodiment, the first light signal received from the first LED 11 does not penetrate deeply through the skin and is therefore more absorbed. This drastically reduces the pulse component in comparison with the first embodiment and therefore increases the contribution from the motion artefact component in the first light signal.

According to another embodiment of the invention, the light signals emitted by the two LEDs have different wavelengths. For example, the LED which is the closest to the photo-detector diode is a blue LED, the other LED being a green LED. As a matter of fact, blue light has a smaller penetration depth than green light. Because the wavelengths are different, the motion artefacts will differ to a larger extent from the green LED to the blue LED.

An optical device according to another embodiment of the invention comprises two LEDs and a photo-detector diode, the light signals emitted by the two LEDs having an identical or similar wavelength, and the two LEDs being situated at different distances from the photo-detector diode. The optical device according to such an embodiment further comprises a temperature sensor for measuring an ambient temperature and a control unit, such as a controller, for selecting one of the two LEDs in dependence on the measured ambient temperature.

Such an embodiment has been implemented based on the following observations. When the distance between the LED and the photo-detector diode increases, then the amount of light received by the photo-detector diode decreases drastically and the pulse amplitude increases. Because the amount of light received by the photo-detector diode is more important at a lower distance, it may be preferable to use the LED which is the closest to the photo-detector diode, however, at the cost of lower pulse amplitude. The situation may become different when the ambient temperature decreases, which leads to a lower blood perfusion into the skin, especially in the superficial layer of the skin. The consequence is that the amplitude of the pulse signal of the first LED that is the closest to the photo-detector diode decreases fast, which is not the same for the second LED that is at a larger distance from the photo-detector diode. As a matter of fact, the light signal emitted by this second LED goes in deeper layers of the skin where blood vessels are larger and which are moreover less affected by a decrease of the ambient temperature, resulting in a much larger pulse signal.

Based on the above, it is proposed an optical device having thus two LEDs situated at different distances from the photo-detector diode, a temperature sensor and a controlling unit to choose automatically one of the two LEDs based on the temperature measured by the temperature sensor. In power save mode, the control unit is configured to switch to the first LED which is the closest to the photo-detector diode. When it is cold outside, e.g. when the ambient temperature measured by the temperature sensor is below a predetermined threshold such as 10° C., the control unit is configured to switch automatically to the second LED which is situated at a larger distance.

In the present specification and claims the word "a" or "an" preceding an element does not exclude the presence of a plurality of such elements. Further, the word "comprising" does not exclude the presence of other elements or steps than those listed.

The inclusion of reference signs in parentheses in the claims is intended to aid understanding and is not intended to be limiting.

From reading the present disclosure, other modifications will be apparent to persons skilled in the art. Such modifications may involve other features which are already known in the art and which may be used instead of or in addition to features already described herein.

The invention claimed is:

1. Optical device for measuring a heart rate of a user, said device comprising:
   two light sources for emitting light into the skin of the user,
   a sensor for receiving light signals from the light emitted by each of the two light sources and reflected through the skin of the user so as to determine the heart rate of the user, wherein the two light sources are situated at different distances from the sensor such that the light signals received from each of the two light sources have a different penetration depth into the skin,
   wherein the device further comprises a temperature sensor for measuring an ambient temperature and a control unit which is configured to select the light source which is farthest from the sensor when the ambient temperature measured by the temperature sensor is below a predetermined threshold.

2. Optical device as claimed in claim 1, wherein the control unit is further configured to select the light source which is the closest to the sensor in power save mode.

3. Optical device as claimed in claim 1, wherein the light signals emitted by two light sources have an identical or similar wavelength.

4. Optical device as claimed in claim 3, wherein the color of the light emitted by the two light sources is green.

5. Optical device as claimed in claim 1, wherein the light signals emitted by two light sources have different wavelengths.

6. Optical device as claimed in claim 5, wherein the color of the light emitted by one light source is green and the color of the light emitted by the other light source is blue and wherein the green light source is placed at a larger distance from the sensor than the blue light source.

7. Optical device as claimed in claim 1, wherein one light source is lift up with respect to the surface of the skin of the user.

8. Optical device as claimed in claim 1, where the light sources are light emitting diodes.

9. Optical device as claimed in claim 1, where the sensor is a photo-detector diode.

10. Optical device as claimed in claim 1, arranged for being worn at the wrist.

11. Optical device as claimed in claim 1, 2, 3, 4, 5, 6, 7, 8, or 9, wherein the light signals emitted by the light sources are pulsed at different times and synchronized with the sensor.

* * * * *